(12) United States Patent  
Jia et al.

(10) Patent No.: US 10,489,909 B2  
(45) Date of Patent: Nov. 26, 2019

(54) METHOD OF AUTOMATICALLY DETECTING MICROANEURYSM BASED ON MULTI-SIEVING CONVOLUTIONAL NEURAL NETWORK

(71) Applicants: SHANGHAI SIXTH PEOPLE'S HOSPITAL, Shanghai (CN); SHANGHAI JIAO TONG UNIVERSITY, Shanghai (CN)

(72) Inventors: Weiping Jia, Shanghai (CN); Bin Sheng, Shanghai (CN); Huating Li, Shanghai (CN); Ling Dai, Shanghai (CN)

(73) Assignees: SHANGHAI SIXTH PEOPLE'S HOSPITAL, Shanghai (CN); SHANGHAI JIAO TONG UNIVERSITY, Shanghai (CN)

( * ) Notice: Subject to any disclaimer, the term of this patent is extended or adjusted under 35 U.S.C. 154(b) by 171 days.

(21) Appl. No.: 15/829,518

(22) Filed: Dec. 1, 2017

(65) Prior Publication Data

US 2018/0165810 A1   Jun. 14, 2018

(30) Foreign Application Priority Data

Dec. 13, 2016  (CN) ........................ 2016 1 1145150

(51) Int. Cl.
*G06K 9/00* (2006.01)
*G06T 7/00* (2017.01)
(Continued)

(52) U.S. Cl.
CPC ........ *G06T 7/0014* (2013.01); *G06K 9/00147* (2013.01); *G06N 3/04* (2013.01);
(Continued)

(58) Field of Classification Search
CPC ................. G06T 7/0014; G06T 7/0012; G06T 2207/30101; G06T 2207/30041;
(Continued)

(56) References Cited

U.S. PATENT DOCUMENTS

2006/0257017 A1* 11/2006 Luo ...................... G06K 9/0061  
382/159  
2011/0026789 A1* 2/2011 Hsu ...................... G06K 9/0061  
382/128

(Continued)

*Primary Examiner* — Van D Huynh  
(74) *Attorney, Agent, or Firm* — Dorsey & Whitney LLP (57) ABSTRACT

A method of automatically detecting microaneurysm based on multi-sieving convolutional neural network (CNN), includes the following steps of: A1), partitioning an image to be detected using random fern and obtaining an auxiliary channel image of the image according to a first partition result; and A2), inputting the auxiliary channel image obtained from step A1) and the image to a multi-sieving CNN training model to perform a detection and obtaining a microaneurysm detection result of the image. The process of establishing the training model includes: B1), using a current microaneurysm diagnostic report as samples and partitioning a lesion image in the microaneurysm diagnostic report using the random fern, and establishing the auxiliary channel image according to a second partition result; B2), comparing the obtained auxiliary channel image with a lesion-marked image of pixels, clarifying the samples according to a comparing result and performing the multi-sieving CNN training.

10 Claims, 4 Drawing Sheets

(51) Int. Cl.
  *G06N 3/04*    (2006.01)
  *G16H 30/40*   (2018.01)
  *G16H 50/20*   (2018.01)
  *G16H 15/00*   (2018.01)

(52) U.S. Cl.
  CPC ......... *G06N 3/0454* (2013.01); *G06T 7/0012* (2013.01); *G16H 30/40* (2018.01); *G16H 50/20* (2018.01); *G06T 2207/20081* (2013.01); *G06T 2207/30041* (2013.01); *G06T 2207/30096* (2013.01); *G06T 2207/30101* (2013.01); *G16H 15/00* (2018.01)

(58) Field of Classification Search
  CPC ........... G06T 2207/20081; G06T 2207/30096; G06K 9/00147; G06N 3/0454; G06N 3/04; G16H 50/20; G16H 30/40; G16H 15/00
  USPC ........................................................ 382/128
  See application file for complete search history.

(56) References Cited

U.S. PATENT DOCUMENTS

| | | | |
|---|---|---|---|
| 2011/0242306 A1* | 10/2011 | Bressler .................. | A61B 3/12 348/78 |
| 2012/0237096 A1* | 9/2012 | Tobin ................... | G06K 9/0061 382/128 |
| 2015/0265144 A1* | 9/2015 | Burlina .................... | A61B 3/10 351/206 |
| 2016/0292856 A1* | 10/2016 | Niemeijer ............. | G06T 7/0012 |
| 2019/0191988 A1* | 6/2019 | Gargeya .................. | A61B 3/12 |

\* cited by examiner

METHOD OF AUTOMATICALLY DETECTING MICROANEURYSM BASED ON MULTI-SIEVING CONVOLUTIONAL NEURAL NETWORK

CROSS REFERENCE TO RELATED APPLICATION

This application claims priority to Chinese Patent Application No. 201611145150.7, entitled "METHOD OF AUTOMATICALLY DETECTING MICROANEURYSM BASED ON MULTI-SIEVING CONVOLUTIONAL NEURAL NETWORK" filed on Dec. 13, 2016, the contents of which are expressly incorporated by reference herein in its entirety.

FIELD OF THE INVENTION

The present disclosure relates to a field of image processing technology, and more particularly relates to a method of automatically detecting microaneurysm based on multi-sieving convolutional neural network (CNN).

BACKGROUND OF THE INVENTION

Microaneurysms (MA) is one of the earliest clinical sign of diabetic retinopathy (DR), thus automatically detection of MA is a critical step to prevent the development of vision threatening eye diseases such as diabetic retinopathy from being blindness. However, in an actual detection, several factors, including the variation in image lighting, the variability of image clarity, occurrence of other red lesion, extremely low contrast and highly variable image background texture, make the accurate detection of MA difficult. For example, normal MA appears as small red dots in color fundus images, while small dot shaped hemorrhage and vessels conjunctions may also appear as small red dots, making the detection challenging for filter-based and morphological-based method. There are three types of methods for the microvascular detection, such as a detection method based on morphology, a detection method based on wavelet transformation and mathematics transformation, and a detection method based on machine learning. The detection method based on machine learning usually adopts a shallow neural network, which supports vector machines and other classifiers. However, whether the method is based on the machine learning, the aforementioned methods are based on the researcher's priori knowledge and strong unproven assumptions that are usually established only in some cases. In addition, the aforementioned methods need to repeatedly consider how to merge the lesion shape information in the segmentation method. As an inimitable symbol of the MA is very low in the fundus image, the detection requires a very sensitive classifier which required to have stability in the cases of image noise interference and other lesions interference. However, the shallow neural network, support vector machine and other classifier cannot meet its requirements of sensitivity and stability.

After reviewing the prior art, "Automated microaneurysm detection method based on double ring filter in retinal fundus images" is published in "SPIE medical imaging" on page 72601N at 2009 by A. Mizutani, which has asserted a graphic filter of Double-Ring-Filter. The filter is used to calculate an average pixel gray value of two different concentric rings. Since the smaller ring covers most of the microvascular area, it will have a smaller average gray value. Rather, the larger ring covers no or only less of the microvascular lesion area, which has a larger average gray value. An area having a larger average gray value in the two different concentric rings will be served as a candidate area. However, the aforementioned method cannot avoid the noise, the small blood vessel whose diameter is similar to the microaneurysm being classified as the microaneurysm, therefore a candidate point needs to be further processed. "Optimal wavelet transform for the detection of the microaneurysm in retina photographs" is published in "IEEE Transactions on Medical Imaging" from pages 1230 to 1241 at 2008 by Quellec, which has asserted the detection method based on the wavelet transformation. The algorithm mainly uses a local template matcher after the wavelet transformation and finds a position of the microaneurysm lesion using direction decent in the region which is matched with the template after an image is transformed based on the wavelet transformation. The aforementioned method uses a two-dimensional symmetrical Gaussian equation to establish a model for the gray map of the microaneurysm, so as to create the template of the microaneurysm. However, the gray distribution of microaneurysm in this method is only observed by a large number of examples, with the development of shooting technology, the actual distribution may be inconsistent with the hypothesis. "Detection and Classification of Microaneurysms Using DTCWT and Log Gabor Features in Retinal Images" is published in "Proceedings of the 3rd International Conference on Frontiers of Intelligent Computing: Theory and Applications (FICTA)" from pages 589 to 596 at 2015 by S. Angadi, which has asserted that a binary tree multiple wavelet transformion and a gabor feature are both used as an image feature based on support vector machine (SVM), texture features are extracted from the image, and the SVM is used as the classifier to classify the images. The SVM is a parameter-sensitive classifier, it is necessary to manually adjust the parameters or search for the best parameters in a high-dimensional space to achieve a good result. Such that it is difficult for the usage of the SVM and the aforementioned method is limited. Furthermore, since the SVM itself can only partition linearly separable problems, if the algorithm is acquired to expand or add new features, which will lead to readjust the parameters and even redesign the nuclear equation.

SUMMARY OF THE INVENTION

It is necessary to provide a method of automatically detecting microaneurysm based on multi-sieving convolutional neural network (CNN) according to various embodiments of the present disclosure.

A method of automatically detecting microaneurysm based on multi-sieving convolutional neural network (CNN) includes:

A1), partitioning an image to be detected using random fern and obtaining an auxiliary channel image of the image according to a first partition result; and inputting the auxiliary channel image obtained from step A1) and the image to a multi-sieving CNN training model to perform a detection and obtaining a microaneurysm detection result of the image;

the multi-sieving CNN training model in step A2) is established according to the following steps of:

B1), using a current microaneurysm diagnostic report as samples and partitioning a lesion image in the microaneurysm diagnostic report using the random fern, and establishing the auxiliary channel image according to a second partition result;

B2), comparing the obtained auxiliary channel image with a lesion-marked image of pixels, clarifying the samples according to a comparing result and performing the multi-sieving CNN training, so as to obtain the multi-sieving CNN training model.

According to an embodiment, the step B1) includes:

B11), using the current microaneurysm diagnostic report as the samples and extracting a text from the diagnostic report to create a lesion label set;

B12), partitioning the lesion image using the random fern and calculating a correlation degree ($d_e(j, t)$) between the partitioned pixels and lesion labels; and B13), establishing the auxiliary channel image of the lesion image according to the correlation degree ($d_e(j, t)$) calculated in step B12).

According to an embodiment, a correlation degree ($d_e(j, t)$) between the partitioned pixels and lesion labels is calculated as follows:

$$d_\varepsilon(j, t) = \sum_{e=1}^{E} \sum_{y=1}^{2L} 1_{\gamma_y^e}(j) 1_k(\langle e, y \rangle)$$

j is a corresponding pixel point, t is a corresponding lesion label, ε is a set of the random fern, $\gamma_y^e$ is an area of a feature space corresponding to an index value y of the random fern $L_e$, k is a set of K partition areas which have a highest association measured value with each of the lesion labels, and <e, y> is a space of a random partition result.

According to an embodiment, the association measured value is defined as follows:

$$f(\gamma_y^e, t):(\gamma_y^e, t) \mapsto R$$

$\gamma_y^e$ is the area of the feature space corresponding to the index value y of the random fern Le; f is a function mapping from the feature space area and the lesion label to a real number.

According to an embodiment, the association measured value is defined as follows:

$$f(\gamma_y^e, t) = \frac{1 + l(\gamma_y^e, t)}{\gamma + \sum_{j=1}^{\tau} l(\gamma_y^e, t_j)}$$

$l(\gamma_y^e, t_j) = \sum_{i=1}^{N} 1_{\gamma_y^e}(i) 1_{c_j}(i)$ indicates a number of super pixels having a label t and mapped to the feature space $f(\gamma_y^e, t)$ in a super pixel set, and γ is a Laplace smoothing control parameter.

According to an embodiment, the association measured value is defined as follows:

$$f(\gamma_y^e, t) = \frac{1 + l(\gamma_y^e, t)}{\gamma + \sum_{j=1}^{\tau} l(\gamma_y^e, t_j)} \times \log_2 \frac{I}{h(\gamma_y^e)}$$

I indicates a total number of images, $h(\gamma_y^e)$ indicates times of the partition $\gamma_y^e$ of the feature space appearing in the images.

According to an embodiment, the step B13) includes:

B131), traversing the pixels of the lesion image and selecting a pixel having highest correlation degree with a current lesion label for the current lesion label;

B132), redefining a gray value corresponding to the lesion label of the pixel selected in st B133), determining whether the current lesion label is a last one in the lesion label set; using a generated gray image as the auxiliary channel image to output when the current lesion label is the last one in the lesion label set; and using a next lesion label as the current lesion label and returning to the step B131) when the current lesion label is not the last one in the lesion label set.

According to an embodiment the step B2) includes:

B21), comparing the obtained auxiliary channel image with the lesion-marked image of the pixels, clarifying the samples as positive samples and negative samples; and B22), randomly selecting the positive samples and the negative samples to perform the multi-sieving CNN training, and stopping the training to obtain the training model when a growth rate of false positive samples in the negative samples remains unchanged.

According to an embodiment, the positive samples includes true positive samples and false negative samples, the negative samples includes false positive samples and true negative samples; the true positive samples are pixels having lesion marked by manual operation and the auxiliary channel image; the false negative samples are pixels having lesion marked by manual operation and without lesion marked by the auxiliary channel image; the false positive samples are pixels having lesion marked by the auxiliary channel image and without lesion marked by manual operation; and the true negative samples are pixels without lesion marked by manual operation and the auxiliary channel image.

According to an embodiment, the step B22) includes:

B221), keeping the number of the positive samples unchanged, randomly selecting the same number of negative samples as the positive samples to add a training sample set to perform the CNN training;

B222), determining whether the number of the obtained false positive samples is greater than the number of the positive samples; randomly sampling the same number of false positive samples as the positive samples to add the training sample set to perform a next round of CNN training when the number of the obtained false positive samples is greater than the number of the positive samples; and returning to the step B223) when the number of the obtained false positive samples is not greater than the number of the positive samples;

B223), adding the obtained false positive samples to the training sample set; and randomly selecting the negative samples to perform the next round of CNN training, wherein the number of the randomly collected negative samples equals to the difference between the number of the positive samples and the number of false positive samples; and B224), determining whether the growth rate of the obtained false positive samples remains unchanged; stopping the training to obtain the training model when the growth rate of the obtained false positive samples remains unchanged; and returning to the step B223) when the growth rate of the obtained false positive samples changed.\

Comparing to the prior art, the present disclosure has the following advantageous effects:

(1) A preliminary diagnosis result can be obtained by partitioning the lesion image using random fern firstly. Furthermore, the multi-sieving CNN model is used to perform a sophisticated partition, and a final diagnosis result can be obtained. The preliminary diagnosis avoids the excessive computation of the subsequent sophisticated partition. The sophisticated partition ensures the accuracy of the detection result, which not only shortens the detection time, but also ensures the accuracy of the detection result.

(2) By the multi-sieving CNN training, the lesion detection of the MA can be ensured to have stability in the cases of image noise interference and other lesions interference.

(3) The text diagnosis results are partitioned as the lesion labels, and the image information and text information are combined, which can use the existing text diagnosis and the corresponding images to excavate an relationship between image features and lesions, thereby providing reference information for the subsequent CNN training, so as to accelerate the convergence of the subsequent CNN training.

(4) The multi-sieving CNN can obtain a better classification result in the case of serious imbalance between the positive and negative training samples, and have a good pertinence to the lesion detection of the microaneurysm, thus ensuring the accuracy of the detection.

(5) The method provided in the present disclosure fuses a plurality of information, which has a universality and can be applied to other lesion detection and partition of other nonmedical images.

BRIEF DESCRIPTION OF THE DRAWINGS

The above objects, features and advantages of the present disclosure will become more apparent by describing in detail embodiments thereof with reference to the accompanying drawings. The components in the drawings are not necessarily drawn to scale, the emphasis instead being placed upon clearly illustrating the principles of the present disclosure. Moreover, in the drawings, like reference numerals designate corresponding parts throughout the views.

FIG. 5a is a graph showing the first iteration result, FIG. 5b is a graph showing the second iteration result.

DETAILED DESCRIPTION OF THE EMBODIMENTS

Embodiments of the invention are described more fully hereinafter with reference to the accompanying drawings, some embodiments of the present disclosure are shown in the accompanying drawings. The various embodiments of the invention may, however, be embodied in many different forms and should not be construed as limited to the embodiments set forth herein. Rather, these embodiments are provided so that this disclosure will be thorough and complete, and will fully convey the scope of the present disclosure to those skilled in the art.

Figure 1:
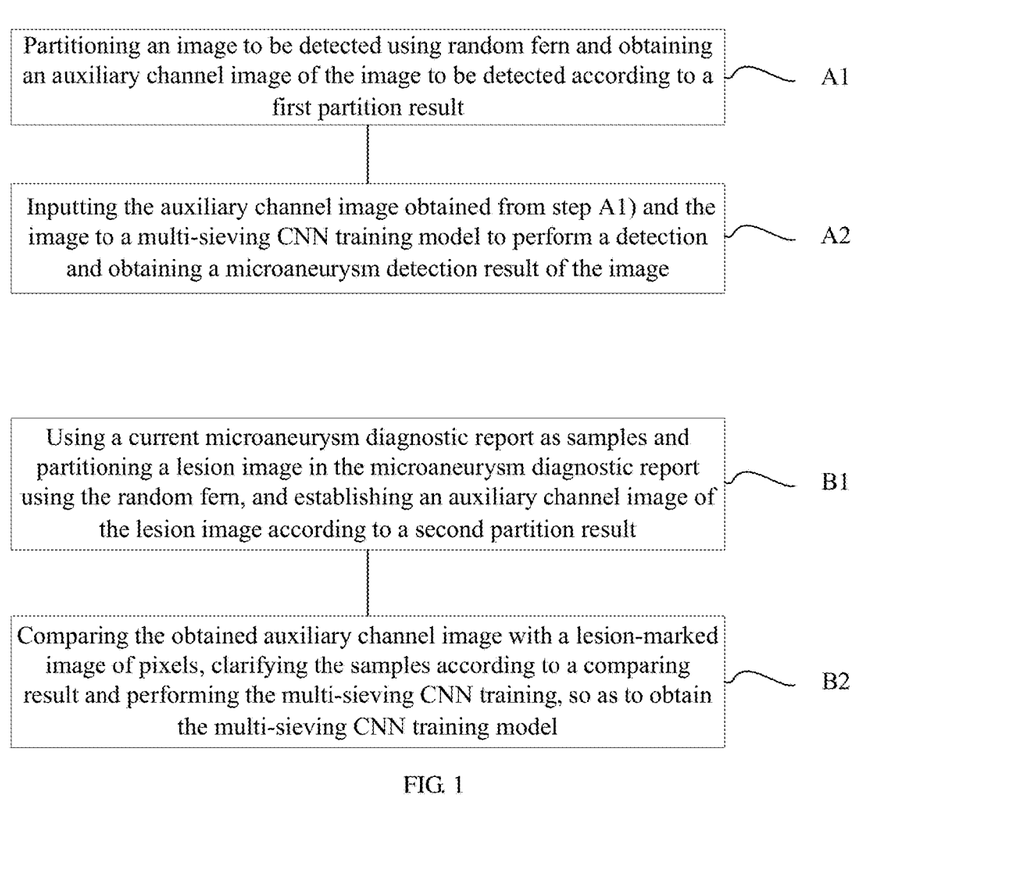
FIG. 1 is a flowchart of a method of automatically detecting microaneurysm based on multi-sieving convolutional neural network (CNN) according to an embodiment.

FIG. 1 is a flowchart of a method of automatically detecting microaneurysm based on multi-sieving convolutional neural network (CNN) according to an embodiment, the method includes the following steps of:

A1), an image to be detected is partitioned using random fern and an auxiliary channel image of the image is obtained according to a first partition result.

The specific process of partitioning an image to be detected using random fern is as follows:

The fern F is defined as a sequence of a functions. If there are L binary functions in F, each binary function $\{L_1, L_2, \ldots, L_L\}$ will produce a bit in F, and the F maps a feature space to $\{1, 2, \ldots, 2^L\}$.

$F(f): f \mapsto \{1, 2, \ldots, 2^L\}$, $F=\{L_1, L_2, \ldots, L_L\}$, which is a function that using a vector f as an input, and using an integer serial number as an output.

$$L(f): f \mapsto \{0, 1\}$$

$$L_1(f) = \begin{cases} 0, \text{ if } (S_i^{subl_1})^T \cdot f^{subl_1} \leq \tau_1 \\ 1, \text{ if } (S_i^{subl_1})^T \cdot f^{subl_1} \leq \tau_1 \end{cases}$$

Specifically, as for the binary function, $S_i^{subl_1}$ is a random sample in a circle on the feature space; $\tau_1$ is a threshold value, which is obtained by randomly sampling from all the $(S_i^{subl_1}) \cdot f^{subl_1}$.

The partition process using the random fern is repeated to generate a set ε of E random ferns, where each of the random ferns includes L binary functions, and the following can be obtained:

$$K\varepsilon: f \mapsto \{1,2,\ldots,2^L\}^E$$

$$\varepsilon(f): f \mapsto \{y_1, y_2, \ldots, y_n\}, y \in \{1,2,\ldots,2^L\}$$

At the same time, each of the feature vector is mapped to the integer vector, and each of the integers corresponds to an index value of a space partitioned using the random fern.

A2), the auxiliary channel image obtained from step A1) and the image to be detected are input to a multi-sieving CNN training model to perform a detection and a microaneurysm detection result of the image is obtained.

Specifically, the multi-sieving CNN training model in step A2) is established according to the following steps of:

B1), a current microaneurysm diagnostic report is used as samples and a lesion image in the microaneurysm diagnostic report is partitioned using the random fern, and the auxiliary channel image is established according to a second partition result. Moreover, the step B1) includes:

B11), the current microaneurysm diagnostic report is used as the samples and a text is extracted from the diagnostic report to create a lesion label set.

Specifically, the step of extracting the text from the diagnostic report to create the lesion label set means to transform a lesion information written in the natural language into a label set. That a label appears in a label set of an image indicates that the image contains the lesion represented by the label. The lesion information written in the natural language is from the text diagnostic report. A lesion name keyword $K_i$ (i∈1, 2, 3, . . . ) appearing in a fundus image is manually extracted from the text diagnostic report, and each of the keyword $K_i$ corresponds to a label i. As for a diagnostic report j, assuming that it corresponds to a fundus image $I_j$, if it contains a keyword $t_i$ when finding keywords from it's text diagnostic report, which indicates that the image $I_j$ is marked with the label i. Such that each of the image $I_j$ in a database corresponds to a label set $T_j$. The text diagnosis results are partitioned as the lesion labels, and the image information and text information are combined, which can use the existing text diagnosis and the corresponding images to excavate an relationship between image features and lesions, thereby providing reference information for the subsequent CNN training, so as to accelerate the convergence of the subsequent CNN training.

B12), the lesion image is partitioned using the random fern and a correlation degree (dε (j, t)) between the partitioned pixels and the lesion labels is calculated.

Specifically, $$d_\varepsilon(j, t) = \sum_{e=1}^{E} \sum_{y=1}^{2^L} 1_{\gamma_y^e}(j) 1_k(\langle e, y \rangle),$$

where j is a corresponding pixel point, t is a corresponding lesion label, ε is a set of the random fern, $\gamma_y^e$ is an area of a feature space corresponding to an index value y of the random fern $L_e$, k is a set of K partition areas which have a highest association measured value with each of the lesion labels, and <e, y> is a space of a random partition result.

For a given super pixel j, it's association with each of the lesion can be calculated and a new vector can be generate according to the aforementioned formula, from which a lesion type with the largest value is selected and the super pixel is considered to contain such the lesion type.

The auxiliary channel image can be obtained according to the calculated correlation degree between the pixels and lesion labels. A gray value corresponding each of the lesion types is defined. As for each of pixel points in an original image, if it contains a lesion type, the pixel point will be assigned a predefined gray value. Such that a gray map will be generated, where different grays correspond to different lesion. The generated gray map will be as input of an automatic diagnosis system to assist in the automatic diagnostic system for accurate detection of microaneurysm.

Furthermore, in order to find the feature space area corresponding to a lesion, an association measured value is defined as follows:

$$f(\gamma_y^e, t):(\gamma_y^e, t) \mapsto R$$

Specifically, $\gamma_y^e$ is the area of the feature space corresponding to an index value y of the random fern $L_e$; f is a function mapping from the feature space area and the lesion label to a real number, which is used to refer to a correlation degree between the corresponding feature area and the lesion. The association measured value is defined as follows:

$$f(\gamma_y^e, t) = \frac{1 + l(\gamma_y^e, t)}{\gamma + \sum_{j=1}^{\tau} l(\gamma_y^e, t_j)}$$

$l(\gamma_y^e, t_j) = \sum_{i=1}^{N} 1_{\gamma_y^e}(i)$ indicates a number of super pixels having a label t and mapped to the feature space $f(\gamma_y^e, t)$ in a super pixel set. γ is a Laplace smoothing control parameter.

On the basis of the association measured value $f(\gamma_y^e, t)$, according to the IF. IDF model, factors that measure the stability of the association measured value are used to solve a noise problem of an area containing only a few super pixel points. The association measured value is as follows after adding factor:

$$f(\gamma_y^e, t) = \frac{1 + l(\gamma_y^e, t)}{\gamma + \sum_{j=1}^{\tau} l(\gamma_y^e, t_j)} \times \log_2 \frac{I}{h(\gamma_y^e)}$$

Specifically, I indicates a total number of images, $h(\gamma_y^e)$ indicates times of the partition $\gamma_y^e$ of the feature space appearing in all the images.

In order to generate a more stable super-pixel lesion type mapping, the k partition areas with a largest association measured value are selected for each of the labels corresponding to the lesion type and are formed as a set.

$$K^t = \{<e_1, y_1>, \ldots, <e_k, y_k>\}$$

Specifically, each of the tuples <e,y> indicates a space $\gamma_y^e$ of a random partition result.

Figure 2:
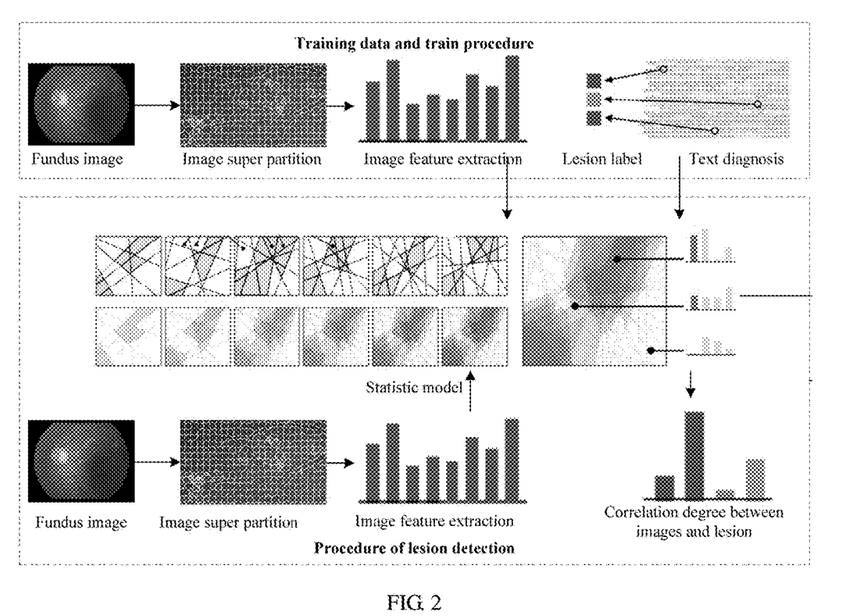
FIG. 2 is block diagram showing a generation of an auxiliary channel image according to an embodiment.

B13), referring to FIG. 2, the auxiliary channel image of the lesion image is established according to the correlation degree ($d_e(j, t)$) calculated in step B12). Moreover, the step B13) includes:

B131), all the pixels of the lesion image is traversed and a pixel having highest correlation degree with a current lesion label is selected.

B132), a gray value corresponding to the lesion label of the pixel selected in step B131) is redefined.

B133), whether the current lesion label is a last one in the lesion label set is determined, a generated gray image is used as he auxiliary channel image to output when the current lesion label is the last one in the lesion label set, and a next lesion label is used as the current lesion label and returning to the step B131) when the current lesion label is not the last one in the lesion label set.

B2), the obtained auxiliary channel image is compared with a lesion-marked image of pixels, the samples are clarified according to a comparing result, the multi-sieving CNN training is performed to obtain the multi-sieving CNN training model. Moreover the step B2) includes:

B21), the obtained auxiliary channel image is compared with the lesion-marked image of the pixels, and the samples are clarified as positive samples and negative samples. Specifically, the positive samples includes true positive samples and false negative samples, the negative samples includes false positive samples and true negative samples. The true positive samples are pixels having lesion marked by manual operation and the auxiliary channel image. The false negative samples are pixels having lesion marked by manual operation and without lesion marked by the auxiliary channel image. The false positive samples are pixels having lesion marked by the auxiliary channel image and without lesion marked by manual operation. The true negative samples are pixels without lesion marked by manual operation and the auxiliary channel image.

B22), the positive samples and the negative samples are randomly selected to perform the multi-sieving CNN training, and the training is stopped to obtain the training model when a growth rate of false positive and the samples in the negative samples remains unchanged. Moreover the step B22) includes:

B221), the number of the positive samples is kept unchanged, the same number of negative samples as the positive samples are randomly selected to add a training sample set to perform the CNN training randomly.

B222), whether the number of the obtained false positive samples is greater than the number of the positive samples is determined, the same number of false positive samples as positive samples are randomly sampled to add the training sample set to perform a next round of CNN training when the number of the obtained false positive samples is greater than the number of the positive samples, and returning to the step B223) when the number of the obtained false positive samples is not greater than the number of the positive samples.

B223), all the obtained false positive samples are added to the training sample set; the negative samples are randomly selected to perform the next CNN training, where the number of the randomly collected negative samples equals to the difference between the number of the positive samples and the number of false positive samples.

B224), the training is stopped to obtain the training model when the growth rate of the obtained false positive samples remains unchanged; and returning to the step B223), when the growth rate of the obtained false positive samples remains changed.

Figure 3:
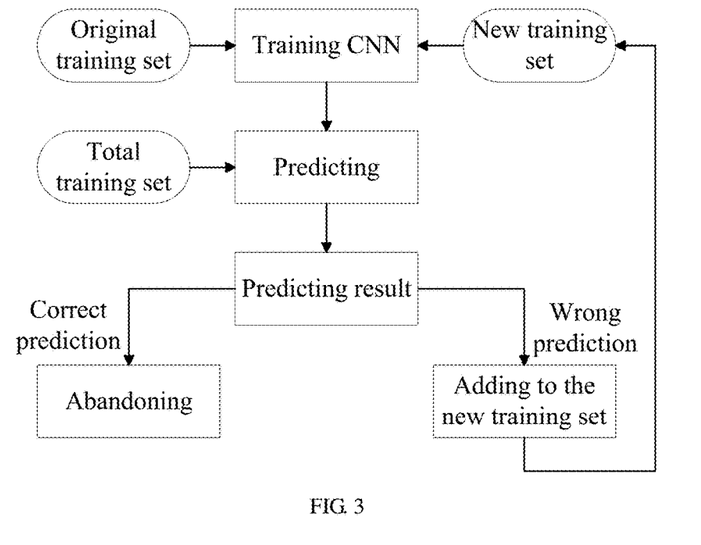
FIG. 3 is a training flowchart of the multi-sieving CNN according to an embodiment.

According to an embodiment, referring to FIG. 3, the specific process of performing the multi-sieving CNN training is: in the first round of training, a small number of positive class samples remain unchanged, the false positive samples with the same number of the positive samples are samples to add the training sample set to perform a CNN training. After training, all training data is input to CNN for prediction. The predictions of this round will generate many false positive (the number of which is much larger than the number of positive samples). Such false positive samples are considered as samples that have not yet been studied well or are difficult for classifiers. At this time, since the false positive samples are still more than the positive samples, the false positive samples are randomly sampled and the same number of false positive samples as the positive samples are selected into the training data set, while keeping the positive samples unchanged in the training data set. At this time, the training and prediction steps in the last round of training are repeated, and the training samples are selected for the next round according to the same strategy. After several training, the number of false positive samples may begin to be less than the number of positive samples. At this time, the original sample selection strategy is adjusted, and all the false positive samples and all the positive samples are selected into the next training set, whist because of the small number of false positive samples, it is necessary to randomly select a certain number of samples from all the negative samples to add the training set, so that the positive samples and negative training in the training set maintain balance.

When the training algorithm is effectively learned and the training begins, each round of training will inevitably reduce the number of erroneously classified samples. As the training process continues to iterate, the new correct classification data points will gradually decrease and may form a dynamic balance with the increased error data points. At this point the algorithm should exit the loop and terminate the training process. Since the continued training has been unable to achieve better performance of the classifier, and may lead to overfitting.

After the training is completed, the training model can be obtained. The image to be detected is randomly partitioned firstly, and then being entered into the training model for training to obtain a test result.

Figure 4:
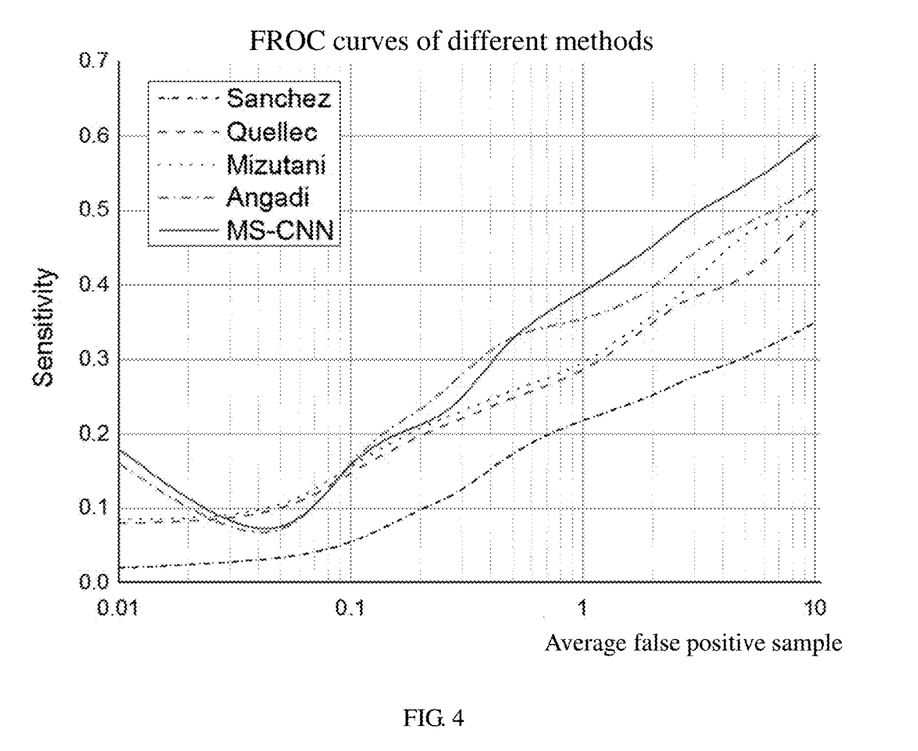
FIG. 4 is a graphic diagram of FROC curves obtained by testing the same data set using different training methods according to an embodiment.

In the illustrated embodiment, 40 obtained images containing manual annotation and corresponding diagnostic fundus lesion images are used to train and test. 20 images are randomly selected as the training set and the remaining images are testing set. The test result is compared with a result of manual annotation. All experiments can be achieved on a personal computer (PC). In the illustrated embodiment, a plurality of methods are implemented to test on the same data set. Referring to FIG. 4, FIG. 4 is a graphic diagram of FROC curves obtained by testing the same data set using different training methods, which shows that the method of multi-sieving CNN training has a greater advantage than the existing methods.

Figure 5:
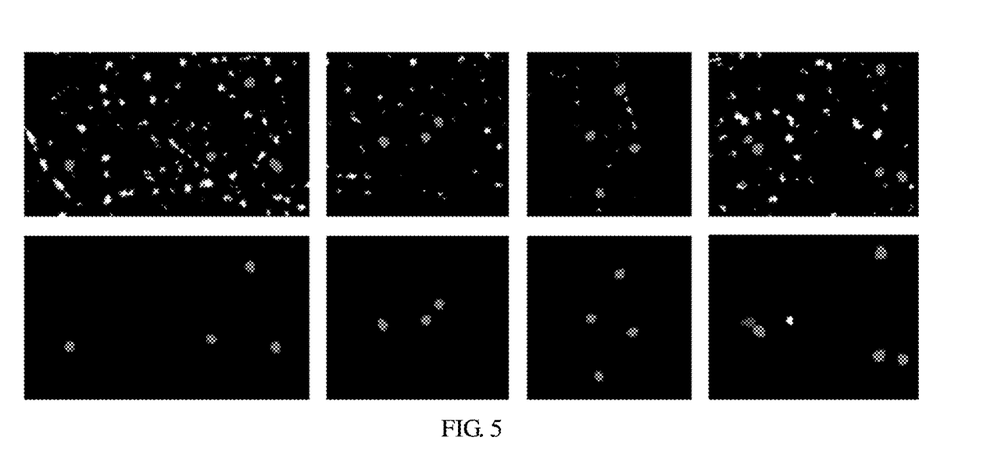
FIG. 5 is a schematic diagram showing a comparison of the results of a first iteration and a second iteration of the multi-sieving CNN, where

In the illustrated embodiment, a plurality of iterative training tests have been performed. According to the result data, in the first iteration of the multi-sieving CNN, precision is 0.997, recall is 0.950, accuracy is 0.321, and a value of F1 is 0.480. In the second iteration of the multi-sieving CNN, precision is 0.999, recall is 0.939, accuracy is 0.321, and a value of F1 is 0.841. FIG. 5 shows the results of multiple iterations, FIG. (5a) shows the result of the first iteration, FIG. (5b) shows the result of the second iteration. The results show that iterative training can greatly improve the performance of the classifier.

Figure 6:
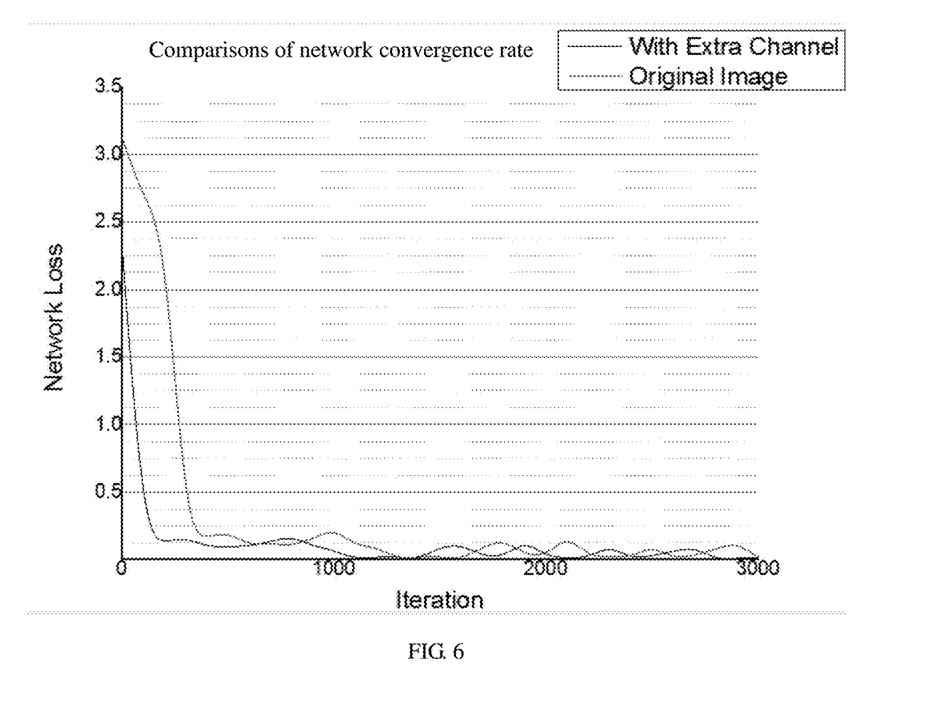
FIG. 6 is a graphic diagram showing a comparison of convergence speed of neural network with a medical report input and without the medical report input.

In the illustrated embodiment, the test results including a medical report learning model or no medical report learning model are compared at the same time. According to the result data, when the CNN includes the medical report learning model, recall is 0.939, accuracy is 0.761, and a value of F1 is 0.841. When the CNN doesn't include the medical report learning model, recall is 0.901, accuracy is 0.741, and a value of F1 is 0.813. Accordingly, the medical report learning model did help the CNN training, thereby improving the performance of classifiers. Referring to FIG. 6, FIG. 6 is a graphic diagram showing a comparison of convergence speed of neural network with a medical report input and without the medical report input. From the point of view of network convergence speed, the input of the medical report information accelerates the network convergence, thereby making the CNN training easier.

According to the aforementioned method of automatically detecting microaneurysm based on multi-sieving CNN, a preliminary diagnosis result can be obtained by partitioning the lesion image using random fern firstly. Furthermore, the multi-sieving CNN model is used to perform a sophisticated partition, and a final diagnosis result can be obtained. The preliminary diagnosis avoids the excessive computation of the subsequent sophisticated partition. The sophisticated partition ensures the accuracy of the detection result, which not only shortens the detection time, but also ensures the accuracy of the detection result. By the multi-sieving CNN training, the lesion detection of the MA can be ensured to have stability in the cases of image noise interference and other lesions interference. In addition, the multi-sieving CNN can get a better classification result in the case of serious imbalance between the positive and negative training samples, and have a good pertinence to the lesion detection of the microaneurysm, therefore ensuring the accuracy of the detection. Moreover, the method provided in the present disclosure fuses a plurality of information, which has a universality and can be applied to other lesion detection and partition of other nonmedical images.

Although the invention is illustrated and described herein with reference to specific embodiments, the invention is not intended to be limited to the details shown. It should be noted that any variation or replacement readily figured out by a person skilled in the art within the technical scope disclosed in the present invention shall all fall within the protection scope of the present invention. Therefore, the protection scope of the present invention shall be subject to the protection scope of the appended claims.

What is claimed is:
1. A method of automatically detecting microaneurysm based on multi-sieving convolutional neural network (CNN), the method comprising:
   A1), partitioning an image to be detected using random fern and obtaining an auxiliary channel image of the image to be detected according to a first partition result; and
   A2), inputting the auxiliary channel image obtained from step A1) and the image to a multi-sieving CNN training model to perform a detection and obtaining a microaneurysm detection result of the image;
   wherein the multi-sieving CNN training model in step A2) is established according to the following steps of:
      B1), using a current microaneurysm diagnostic report as samples and partitioning a lesion image in the microaneurysm diagnostic report using the random fern, and establishing an auxiliary channel image of the lesion image according to a second partition result; and
      B2), comparing the obtained auxiliary channel image with a lesion-marked image of pixels, clarifying the samples according to a comparing result and performing the multi-sieving CNN training, so as to obtain the multi-sieving CNN training model.
2. The method of claim 1, wherein the step B1) comprises:
   B11), using the current microaneurysm diagnostic report as the samples and extracting a text from the diagnostic report to create a lesion label set;
   B12), partitioning the lesion image using the random fern and calculating a correlation degree ($d_e(j, t)$) between the partitioned pixels and lesion labels; and
   B13), establishing the auxiliary channel image of the lesion image according to the correlation degree ($d_e(j, t)$) calculated in step B12).
3. The method of claim 2, wherein the correlation degree ($d_e(j, t)$) is calculated as follows:

$$d_e(j, t) = \sum_{e=1}^{E} \sum_{y=1}^{2L} 1_{\gamma_y^e}(j) 1_k(\langle e, y \rangle)$$

wherein j is a corresponding pixel point, t is a corresponding lesion label, $\varepsilon$ is a set of the random fern, $\gamma_y^e$ is an area of a feature space corresponding to an index value y of the random fern $L_e$, k is a set of K partition areas which have a highest association measured value with each of the lesion labels, and $\langle e, y \rangle$ is a space of a random partition result.
4. The method of claim 3, wherein the association measured value is defined as follows:

$$f(\gamma_y^e, t) : (\gamma_y^e, t) \mapsto R$$

wherein $\gamma_y^e$ is the area of the feature space corresponding to the index value y of the random fern Le; f is a function mapping from the feature space area and the lesion label to a real number.
5. The method of claim 3, wherein the association measured value is defined as follows:

$$f(\gamma_y^e, t) = \frac{1 + l(\gamma_y^e, t)}{\gamma + \sum_{j=1}^{\tau} l(\gamma_y^e, t_j)}$$

wherein $l(\gamma_y^e, t_j) = \sum_{i=1}^{N} 1_{\gamma_y^e}(i)$ indicates a number of super pixels having a label t and mapped to the feature space $f(\gamma_y^e, t)$ in a super pixel set, and $\gamma$ is a Laplace smoothing control parameter.
6. The method of claim 3, wherein the association measured value is defined as follows:

$$f(\gamma_y^e, t) = \frac{1 + l(\gamma_y^e, t)}{\gamma + \sum_{j=1}^{\tau} l(\gamma_y^e, t_j)} \times \log_2 \frac{I}{h(\gamma_y^e)}$$

wherein I indicates a total number of images, $h(\gamma_y^e)$ indicates times of the partition $\gamma_y^e$ of the feature space appearing in the images.
7. The method of claim 3, wherein the step B13) comprises:
   B131), traversing the pixels of the lesion image and selecting a pixel having highest correlation degree with a current lesion label for the current lesion label;
   B132), redefining a gray value corresponding to the lesion label of the pixel selected in step B131); and
   B133), determining whether the current lesion label is a last one in the lesion label set; using a generated gray image as the auxiliary channel image to output when the current lesion label is the last one in the lesion label set; and using a next lesion label as the current lesion label and returning to the step B131) when the current lesion label is not the last one in the lesion label set.
8. The method of claim 1, wherein the step B2) comprises:
   B21), comparing the obtained auxiliary channel image with the lesion-marked image of the pixels, clarifying the samples as positive samples and negative samples; and
   B22), randomly selecting the positive samples and the negative samples to perform the multi-sieving CNN training, and stopping the training to obtain the training model when a growth rate of false positive samples in the negative samples remains unchanged.
9. The method of claim 8, wherein the positive samples comprise true positive samples and false negative samples, the negative samples comprise false positive samples and true negative samples; wherein the true positive samples are pixels having lesion marked by manual operation and the auxiliary channel image; the false negative samples are pixels having lesion marked by manual operation and without lesion marked by the auxiliary channel image; the false positive samples are pixels having lesion marked by the auxiliary channel image and without lesion marked by manual operation; and the true negative samples are pixels without lesion marked by manual operation and the auxiliary channel image.
10. The method of claim 9, wherein the step B22) comprises:
   B221), keeping the number of the positive samples unchanged, randomly selecting the same number of negative samples as the positive samples to add a training sample set to perform the CNN training;
   B222), determining whether the number of the obtained false positive samples is greater than the number of the positive samples; randomly sampling the same number of false positive samples as the positive samples to add the training sample set to perform a next round of CNN training when the number of the obtained false positive samples is greater than the number of the positive samples; and returning to the step B223) when the number of the obtained false positive samples is not greater than the number of the positive samples;

B223), adding the obtained false positive samples to the training sample set; and randomly selecting the negative samples to perform the next round of CNN training, wherein the number of the randomly collected negative samples equals to the difference between the number of the positive samples and the number of false positive samples; and B224), determining whether the growth rate of the obtained false positive samples remains unchanged; stopping the training to obtain the training model when the growth rate of the obtained false positive samples remains unchanged; and returning to the step B223) when the growth rate of the obtained false positive samples changed.

* * * * *